US012226583B2

(12) United States Patent
Liu et al.

(10) Patent No.: US 12,226,583 B2
(45) Date of Patent: Feb. 18, 2025

(54) SENSING FOR RESPIRATORY CIRCUITS

(71) Applicant: Fisher & Paykel Healthcare Limited, Auckland (NZ)

(72) Inventors: Po-Yen Liu, Auckland (NZ); Paul James Tonkin, Auckland (NZ); Salman Mansoor Javed, Auckland (NZ); Chenjie Yan, Auckland (NZ); Peter Alan Seekup, Auckland (NZ); Anton Petrochenko, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 34 days.

(21) Appl. No.: 18/448,477

(22) Filed: Aug. 11, 2023

(65) Prior Publication Data
US 2024/0042158 A1     Feb. 8, 2024

Related U.S. Application Data

(63) Continuation of application No. 16/319,631, filed as application No. PCT/NZ2017/050101 on Jul. 24, 2017, now Pat. No. 11,766,537.
(Continued)

(51) Int. Cl.
  *A61M 16/10*     (2006.01)
  *A61M 16/00*     (2006.01)
  (Continued)

(52) U.S. Cl.
  CPC .... *A61M 16/1045* (2013.01); *A61M 16/0066* (2013.01); *A61M 16/024* (2017.08);
  (Continued)

(58) Field of Classification Search
  CPC .......... A61M 16/1045; A61M 16/0066; A61M 16/024; A61M 16/161; A61M 16/0003;
  (Continued)

(56) References Cited

U.S. PATENT DOCUMENTS 3,572,317 A    3/1971   Wade
4,616,325 A    10/1986  Heckenbach et al.
(Continued)

FOREIGN PATENT DOCUMENTS

CN    104955510 A     5/2017
DE    102010045193 A1  3/2012
(Continued)

OTHER PUBLICATIONS

Search Report in corresponding International Patent Application No. PCT/NZ2017/050101, dated Oct. 30, 2017, in 5 pages.

*Primary Examiner* — Elliot S Ruddie
(74) *Attorney, Agent, or Firm* — Knobbe Martens Olson & Bear LLP

(57) ABSTRACT

Some embodiments provide a breathing assistance apparatus comprising a conduit for conveying gases therein, the conduit comprising circuitry. The circuitry may comprise at least one heater wire part to heat gases in the conduit, in use, and at least one sensor wire part comprising at least one sensor for monitoring a parameter of the gases in the conduit. There is also provided a controller to control provision of AC power or AC voltage to the heater wire part; and control selective reading of the sensor. The controller may be configured to read the sensor at or about a particular portion of the AC power waveform provided to the heater wire part.

20 Claims, 6 Drawing Sheets

Related U.S. Application Data

(60) Provisional application No. 62/365,664, filed on Jul. 22, 2016.

(51) Int. Cl.
*A61M 16/08* (2006.01)
*A61M 16/16* (2006.01)
*H05B 1/02* (2006.01)

(52) U.S. Cl.
CPC ....... *A61M 16/161* (2014.02); *A61M 16/0003* (2014.02); *A61M 16/0816* (2013.01); *A61M 16/0875* (2013.01); *A61M 2205/33* (2013.01); *H05B 1/025* (2013.01)

(58) Field of Classification Search
CPC .......... A61M 16/0816; A61M 16/0875; A61M 2205/33; A61M 16/1095; A61M 2205/3331; A61M 2205/50; A61M 2205/6054; A61M 16/1085; A61M 16/109; A61M 16/16; A61M 2016/0027; A61M 2016/0033; A61M 2016/1025; A61M 2205/14; A61M 2205/3368; A61M 2205/6027; A61M 2240/00; H05B 1/025; A61G 11/00

See application file for complete search history.

(56) References Cited

U.S. PATENT DOCUMENTS

| | | | | |
|---|---|---|---|---|
| 4,945,305 A | * | 7/1990 | Blood | G01B 7/14 |
| | | | | 324/207.17 |
| 5,043,560 A | | 8/1991 | Masreliez | |
| 5,558,084 A | * | 9/1996 | Daniell | A61M 16/1085 |
| | | | | 261/130 |
| 6,647,289 B2 | | 11/2003 | Prutchi | |
| 7,775,210 B2 | | 8/2010 | Schobel et al. | |
| 8,063,343 B2 | | 11/2011 | McGhin et al. | |
| 8,692,167 B2 | | 4/2014 | Hedmann et al. | |
| 8,827,993 B2 | | 9/2014 | Govari et al. | |
| 11,766,537 B2 | | 9/2023 | Liu et al. | |
| 2002/0040192 A1 | | 4/2002 | Prutchi | |
| 2003/0154977 A1 | * | 8/2003 | White | A61M 16/16 |
| | | | | 128/201.13 |
| 2007/0284361 A1 | | 12/2007 | Nadjafizadeh et al. | |
| 2008/0105257 A1 | | 5/2008 | Klasek et al. | |
| 2009/0107982 A1 | * | 4/2009 | McGhin | A61M 16/024 |
| | | | | 261/139 |
| 2009/0229606 A1 | | 9/2009 | Tang et al. | |
| 2011/0230779 A1 | | 9/2011 | Titchener et al. | |
| 2013/0338520 A1 | | 12/2013 | Govari et al. | |
| 2014/0216459 A1 | | 8/2014 | Vos et al. | |

FOREIGN PATENT DOCUMENTS

| | | | | |
|---|---|---|---|---|
| DE | 102013000489 A1 | 7/2014 | | |
| EP | 0418378 B1 | 10/1994 | | |
| EP | 0535952 B1 | 12/1997 | | |
| JP | H06-023051 A | 2/1994 | | |
| JP | 2004-187951 A | 7/2004 | | |
| NZ | 212163 A | 2/1988 | | |
| WO | WO-2014077706 A1 | * | 5/2014 | ............ A61G 11/00 |
| WO | WO 2018/217105 A1 | 11/2018 | | |

* cited by examiner

SENSING FOR RESPIRATORY CIRCUITS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure generally relates to systems, apparatus and methods for providing humidified gases to users, and more particularly to applications thereof for use with respiratory circuits for humidification systems that involve both sensing and driving or powering of one or more elements, such as a heater coil.

Description of Related Art

Many gas humidification systems deliver heated and humidified gases for various medical procedures, including respiratory treatment, laparoscopy, and the like. These systems can be configured to control temperature, humidity and flow rates using feedback from sensors. To maintain desirable properties upon delivery to a user, a breathing circuit can have heaters associated with gas conduits where the heaters provide heat to the gas as it flows to and/or from the user. The conduit heaters can be controlled to provide heat to the gas so that the gas arrives to the user having desirable properties such as temperature and/or humidity. A humidification system can include a temperature sensor to provide feedback to a humidification controller which can adjust and/or modify power delivered to the conduit heaters to achieve a target temperature at a location along an associated conduit. Other sensors may additionally or alternatively be provided that, for example, measure any one or more of flow, pressure, or humidity, or other properties of gas and/or of one or more components of the system, such as a patient interface or conduit.

Some example respiratory circuit components are disclosed in PCT Application No. PCT/NZ2015/050028 entitled "MEDICAL TUBES FOR RESPIRATORY SYSTEMS," filed Mar. 17, 2015 and incorporated herein by reference in its entirety.

PCT Application No. PCT/NZ2013/000208 entitled "ZONE HEATING FOR RESPIRATORY CIRCUITS," filed Nov. 14, 2014 and incorporated herein by reference in its entirety, discloses respiratory circuits for humidification systems. More particularly, arrangements are described for monitoring parameters within a humidification system and adjusting operation thereof based at least in part thereon. For example, a temperature of gases in an inspiratory conduit of a respiratory circuit may be monitored and power supplied to a heater wire for heating gases in the inspiratory conduit adjusted accordingly.

According to some embodiments disclosed in PCT Application No. PCT/NZ2013/000208, sensor and heater wires terminate at one end of a conduit, at or proximate a cuff. This arrangement can conveniently provide for pneumatic connection of the conduit to a source of gases while at the same time establishing electrical connections between the heater and sensor wires and wider control/power circuitry. Further, the heater and sensor wires are disclosed as being positioned adjacent one another along at least a portion of the length of the tube and being connected to common circuit boards. While this arrangement can reduce the total number of components and simplify manufacture, it has been found that the power supplied to the heater wires creates noise that affects the accuracy of readings from sensors connected to the sensor wires. For infant, multi-zone embodiments disclosed in PCT/NZ2013/000208, when the patient end temperature set point is near 40° C., an error in the region of ±0.3° C. may be introduced and for adult tube embodiments, around ±0.15° C. Any possible reduction in these errors is desirous to improve performance of the system as a whole, especially humidification aspects thereof.

SUMMARY

The systems, methods and devices described herein have innovative aspects, no single one of which is indispensable or solely responsible for their desirable attributes. Without limiting the scope of the claims, some of the advantageous features will now be summarized.

The invention is generally described herein with reference or application to inspiratory limbs. However, the invention is not limited thereto and has wider application. For example, it may be applied to expiratory limbs and/or limbs used for the purposes of providing and/or removing gases etc during insufflation procedures. Hence reference to inspiratory limb is by way of reference only.

According to one aspect of the invention there is provided a controller for a breathing assistance apparatus, the breathing assistance apparatus comprising a conduit for conveying gases therein, the conduit comprising circuitry, the circuitry comprising at least one heater wire part to heat gases in the conduit, in use, and at least one sensor wire part comprising at least one sensor for monitoring a parameter of the gases in the conduit, in use, the controller being configured to:
  control provision of AC power or AC voltage to the heater wire part; and
  control selective reading of the sensor,
  wherein the controller is configured to read the sensor at or about a particular portion of the AC power waveform provided to the heater wire part.

The controller may be arranged such that said particular portion of the AC power or voltage waveform commences at or about or after a first zero crossing of the AC power or voltage waveform, preferably a falling zero crossing, and at or before a second zero crossing of the AC power or voltage waveform, the first and second zero crossings being consecutive zero crossings of the same type.

The controller may be configured to control repeating said selective reading of the sensor, between a third and a fourth zero crossing, the second, third and fourth zero crossings being consecutive zero crossings of the same type.

The controller may comprise or be communicatively couplable to a monitor to monitor the AC power or voltage waveform, wherein the controller controls when to selectively read the sensor based at least in part on a signal indicative of or derived from the monitored AC power or voltage waveform. The controller may be configured to use the monitor to detect a zero crossing of the AC power or voltage waveform, preferably a falling zero crossing. The controller may be configured to use the monitor to detect a portion of the AC power or voltage waveform other than a zero crossing. The controller may be adapted to establish a timing of a zero crossing based at least in part on a timing of the detected portion of the AC power or voltage waveform that is not a zero crossing.

The controller may be adapted to establish, at least in part, a timing of the particular portion of the AC power or voltage waveform based at least in part on one or more known and/or detected characteristics of the AC power waveform. Said characteristic(s) of the AC power or voltage waveform may comprise a frequency thereof.

The at least one heater wire part may comprise at least one heater wire connectable to said AC power or voltage. There may be two or four said heater wires.

The at least one sensor wire part may comprise at least one sensor wire. There may be two said sensor wires. At least a portion of said sensor wire(s) may be positioned adjacent at least a corresponding portion of said heater wire(s). The heater wire part and the sensor wire part may comprise independent circuits.

The controller may comprise or be coupled to a multiplexer, wherein the multiplexer is coupled to or configured to be coupled to the sensor wire part. The multiplexer may be coupled to a plurality of sensor wires to enable reading of corresponding sensors coupled to the sensor wires. The controller may be configured to reset the multiplexer at a positive rising edge of the AC power or voltage waveform and/or during a positive phase of the AC power or voltage waveform. The controller may be configured to use the multiplexer to read the sensor(s) during a falling edge of the AC power or voltage waveform.

The controller may comprise or be communicatively coupled to a memory to store information relating to the AC power or voltage waveform, such as phase information, and/or information relating to the sensor(s) of the sensor wire part.

The controller may comprise at least two sensors, wherein the controller is configured to control reading of a first of said sensors at or about or after a first zero crossing of the AC power or voltage waveform, preferably a falling zero crossing, and at or before a second zero crossing of the AC power or voltage waveform, the first and second zero crossings being consecutive zero crossings of the same type, and wherein the controller is configured to control reading of a second of said sensors at or about or after a third zero crossing and at or before a fourth zero crossing, the first, second, third and fourth zero crossings being consecutive zero crossings of the same type.

The conduit may comprise first and second segments or parts that are connectable together to provide an elongated conduit, wherein the controller is configured to receive a signal indicative of a presence and/or absence of the first and/or second segment and implement control dependent on which segment(s) are present and/or absent. If only the first segment is determined to be present, the controller may adopt a first mode, the first mode preferably being adapted for adult users and/or applications in which the environmental conditions are substantially the same along the length of the conduit. The controller may be configured to control application of power to the at least one heater wire part such that:
the waveform thereof transitions from flat to the negative half of a full cycle, and/or
the waveform thereof transitions from the positive half of a full cycle to flat.
If the second segment is determined to be present, the first segment may comprise a first heater wire part and the second segment comprises a second heater wire part, wherein the controller may be configured to control selective application of power to the first heater wire part during a first time period and to control selective application of power to both the first and second heater wire parts and/or to the second heater wire part only in a second time period.

The controller may be adapted to control application of power:
to the first heater wire part such that the waveform thereof transitions from flat to the first of two positive half cycles and/or to flat following two positive half cycles, and/or
to the second heater wire part such that the waveform thereof transitions from flat or off to the first of two negative half cycles and/or to flat following two negative half cycles, and/or
to both heater wire parts such that the waveform thereof transitions from flat or off to the first of two negative half cycles and/or to flat following two negative half cycles.

The controller may be adapted to determine a frequency of the AC power or voltage.

According to another aspect of the invention, there is provided a breathing assistance apparatus comprising:
a conduit for conveying gases therein, the conduit comprising circuitry, the circuitry comprising:
at least one heater wire part to heat gases in the conduit, in use; and
at least one sensor wire part comprising at least one sensor for monitoring a parameter of the gases in the conduit; and
the controller of any one of the above statements.

At least one heater wire part and/or said at least one sensor wire part may terminate at or proximate to a first end of the conduit, preferably within 20 mm of an end of the conduit, more preferably within 10 mm of an end of the conduit, and more preferably still, within 5 mm of an end of the conduit, said end being the patient end of the tube, in use.

The at least one heater wire part and/or said at least one sensor wire part may be coupled to a printed circuit board, PCB. The PCB may be positioned inside and/or about and/or within a wall forming the conduit. The PCB may be provided at or proximate to a second end of the conduit. The or at least one said sensor may be mounted on or to the PCB.

The heater wire(s) may be associated with a least a portion of a length of the conduit by being provided therein and/or thereabout and/or within a wall forming the conduit.

The sensor wire(s) may be associated with a least a portion of a length of the conduit by being provided therein and/or thereabout and/or within a wall forming the conduit.

The breathing assistance apparatus may comprise two said heater wires and two said sensor wires, the wires being provided in or embedded in a wall of the conduit and spirally wound to be arranged in the sequence heater wire 1, sensor wire 1, sensor wire 2 and heater wire 2.

According to another aspect of the invention there is provided a respiratory humidification system comprising:
the controller of any one of the above statements; and/or
the breathing assistance apparatus of any of the above statements.

According to a further aspect of the invention there is provided a method of respiratory humidification comprising:
controlling provision of AC power or voltage to a heater wire part of a medical tube; and
controlling selective reading of a sensor, provided in or coupled to or otherwise associated with the medical tube, at or about a particular portion of the AC power or voltage waveform provided to the heater wire part.

A medical conduit for use as the conduit referred to in any one of the above statements.

Some embodiments provide for an inspiratory limb for a breathing circuit and/or systems and/or methods including an inspiratory limb. The inspiratory limb described herein is particularly useful or applicable to situations where heated and humidified gases are conveyed therethrough. According to some embodiments, the heated and humidified gases may pass through two distinct environments. This can be a problem, for example, in infant incubators where the temperature is significantly higher than the surrounding environment or where a portion of the conduit delivering the gases to the patient is under a blanket. Some embodiments disclosed herein, however, can be used in any environment where heated and/or humidified gas is delivered to a patient and are not limited to uses where the inspiratory limb passes through two distinct environments.

The inspiratory limb can include a first segment of the inspiratory limb that comprises a first structure forming a conduit, the conduit configured to transport a humidified gas, and wherein the first segment of the inspiratory limb includes a first heater wire part or circuit. The inspiratory limb can include a second segment of the inspiratory limb that comprises a second structure forming a conduit configured to transport the humidified gas, wherein the second structure is configured to mechanically couple or be otherwise joined to or made integral with the first structure of the first segment to form an extended conduit for the humidified gas and wherein the second segment of the inspiratory limb includes a second heater wire part or circuit. The inspiratory limb can include an intermediate connector that includes a connection circuit that electrically couples the first heater wire circuit to the second heater wire circuit, wherein the intermediate connector can be coupled to a patient-end of the first segment of the inspiratory limb and a chamber-end of the second segment of the inspiratory limb to form a single conduit for the humidified gases. The intermediate connector can be covered by a portion of the first segment of the inspiratory limb, a portion of the second segment of the inspiratory limb, or a portion of both the first and second segments of the inspiratory limb such that the intermediate connector is internal to the inspiratory limb.

The inspiratory limb can be configured to operate in two heating modes. In a first heating mode, electrical power passes through the intermediate connector to provide power to the first heater wire circuit without providing power to the second heater wire circuit. In a second heating mode, electrical power passes through the intermediate connector to provide power to both the first heater wire circuit and the second heater wire circuit. For example, the intermediate connector can include electrical components configured to direct electrical power along different paths based at least in part on a direction of current flow and/or a polarity of voltage. The intermediate connector can include conductive tracks which can provide a short (e.g., a direct electrical connection with no intervening electrical components) between one or more wires in the first heater wire circuit and one or more wires in the second heater wire circuit. The intermediate connector can include conductive tracks which electrically couple one or more wires in the first heater wire circuit to one or more wires in the second heater wire circuit, where the conductive tracks include electrical components such as, for example and without limitation, diodes, transistors, capacitors, resistors, logic gates, integrated circuits, or the like. In certain embodiments, the intermediate connector includes a diode electrically coupled to both the first heater wire circuit and the second heater wire circuit. In certain embodiments, the inspiratory limb can further comprise a first sensor part or circuit having a first sensor positioned at the intermediate connector. In certain embodiments, the inspiratory limb further comprises a second sensor circuit having a second sensor positioned at a patient-end connector, the patient-end connector being positioned at a patient-end of the second segment of the inspiratory limb. The inspiratory limb can be configured to operate in two sensing modes. In a first sensing mode, signals from the first sensor are received without receiving signals from the second sensor. In a second sensing mode, signals from the second sensor are received without receiving signals from the first sensor. In some embodiments, sensing includes receiving signals from both the first and second sensors in parallel. In such embodiments, an algorithm can determine a parameter measured by the first sensor based at least in part on the signals received in parallel from both the first and second sensors. In certain embodiments, the intermediate connector includes a diode electrically coupled to both the first sensor circuit and the second sensor circuit. The patient-end connector can be configured to provide electrical connections for the second sensor circuit. Similarly, the patient-end connector can be configured to provide electrical connections for the second heater wire circuit. The sensors can be temperature sensors, humidity sensors, flow sensors, or the like. The first and second sensors can be sensors configured to measure one or more parameters, such as temperature, humidity, flow rate, oxygen percentage, or the like. In some embodiments, the first and second sensors are configured to measure at least one like parameter (e.g., temperature, humidity, flow rate, etc.). In some embodiments, more than two sensors can be included and can be positioned at the intermediate connector and/or the patient-end connector.

Some embodiments provide for a respiratory humidification system with an inspiratory limb and a controller. The inspiratory limb can include a first segment having a first heater wire part or circuit, a second segment having a second heater wire part or circuit, an intermediate connector having a connector circuit configured to electrically couple the first heater wire circuit to the second heater wire circuit, a first sensor positioned at a patient-end of the first segment, and a second sensor positioned at a patient-end of the second segment. The controller can be adapted to selectively switch between a first mode and a second mode wherein in the first mode the controller provides electrical power to the first heater wire circuit through the connector circuit and in a second mode the controller provides electrical power to the first and second heater wire circuits. In certain embodiments, the respiratory humidification system switches between modes based at least in part on input from one or both sensors. In certain embodiments, the switching is done based at least in part on parameters including one or more of temperature, flow, humidity, power, or any combination of these. The parameters can be derived or obtained directly from the first sensor, the second sensor, or a combination of both sensors. In certain embodiments, the first and second modes are defined by a direction of current flow or a polarity of voltage provided by a power source. In some embodiments, the respiratory humidification system can include more than two sensors which provide input used to control heating of the inspiratory limb.

Some embodiments provide for a dual limb circuit that can include an inspiratory limb. Such an inspiratory limb can include a first segment having a first heater wire part or circuit, a second segment of the inspiratory limb having a second heater wire part or circuit, an intermediate connector having a connector circuit configured to electrically couple the first heater wire circuit to the second heater wire circuit, a first sensor positioned at a patient-end of the first segment, and a second sensor positioned at a patient-end of the second segment. The dual limb circuit can also include an expiratory limb with an expiratory heater wire circuit. The dual limb system can further include an interface connected to the inspiratory limb and the expiratory limb. The dual limb system can further include a controller adapted to selectively switch between a first mode and a second mode wherein in the first mode the controller provides electrical power to the first heater wire circuit through the connector circuit and in a second mode the controller provides electrical power to the first and second heater wire circuits. In certain embodiments, heating of the expiratory limb is performed using the expiratory heater wire circuit independent of the heating of the inspiratory limb using the first and second heater wire circuits. In certain embodiments, the expiratory limb is powered in parallel with the first heater wire circuit in the first segment of the inspiratory limb and/or in parallel with the first and second heater wire circuits. In certain embodiments, the expiratory limb can be designed to be powered in only the first mode, only the second mode, or in both the first mode and in the second mode. In certain embodiments, the interface is connected via a wye-piece. Any suitable patient interface can be incorporated. Patient interface is a broad term and is to be given its ordinary and customary meaning to a person of ordinary skill in the art (that is, it is not to be limited to a special or customized meaning) and includes, without limitation, masks (such as tracheal mask, face masks and nasal masks), cannulas, and nasal pillows.

In some embodiments, a segmented inspiratory limb is provided, wherein the structure of the segments comprise an elongate tube. The elongate tubes can include a first elongate member comprising a hollow body spirally wound to form at least in part a conduit having a longitudinal axis, a lumen extending along the longitudinal axis, and a hollow wall surrounding the lumen. The elongate tubes can include a second elongate member spirally wound and joined between adjacent turns of the first elongate member, the second elongate member forming at least a portion of the lumen of the elongate tube. In certain implementations, the first elongate member forms in longitudinal cross-section a plurality of bubbles with a flattened surface at the lumen. In certain implementations, adjacent bubbles are separated by a gap above the second elongate member. In certain implementations, adjacent bubbles are not directly connected to each other. In certain implementations, the plurality of bubbles has perforations.

In some embodiments, a medical conduit, such as an inspiratory limb, is provided that comprises a conduit, a connector or cuff connected to one end of the conduit for pneumatically coupling to a source of gases, a heater wire part, a sensor wire part, and an outlet for conveying gases towards a desired destination. For example, the outlet may comprise a connector or cuff for connecting to a patient interface. The heater wire part may each comprise one or more heater wires running at least a portion of the length of the conduit so as to heat gases as they flow through the conduit. Similarly, one or more sensor wires may run at least a portion of the length of the conduit, coupling a sensor to a control unit. While sensors may be positioned at any point, it is often desirable to include a temperature sensor at or proximate to a patient-end of the conduit so as to obtain an accurate indication of the temperature of gases delivered to a patient. Consequently, some embodiments provide for both heater wire(s) and sensor wire(s) to run the complete or substantially the complete length of the conduit. According to some embodiments, the patient-end of the heater wire part and the sensor wire part are connected to a common circuit board. One or more sensors may be mounted to the board and read using the sensor wire part.

In some embodiments, the heater wire part is connected to an AC supply and the sensor wire part is also coupled thereto so as to enable selective reading of sensor(s) comprised in or coupled to the sensor wire part. According to some embodiments, a waveform of the AC supply is monitored and/or known properties of the waveform are used to detect or determine the timing of one or more zero crossings (preferably falling zero crossings) of the AC supply waveform. According to such embodiments, the sensor(s) are preferably read at or about or after a zero crossing. Preferably, the sensor is read within ±25 ms of a zero crossing, more preferably ±15 ms, more preferably 10 ms, more preferably ±5 ms, and more preferably still by about ±3 ms. According to some presently preferred embodiments, the reading is taken with ±150 µs of a zero crossing, more preferably ±100 µs of a zero crossing and more preferably still ±50 µs of a zero crossing. The reduced ranges may be achieved by using interrupts to measure the sensor. These ranges are applicable to other references to at or about or after a zero crossing but for sake of brevity have not been repeated. Further, the sensor(s) are preferably read prior to the subsequent zero crossing of the same type (i.e. rising or falling). Reading of the sensor(s) may be repeated as desired, preferably with the zero crossing relationship maintained. Controlling reading of the sensor(s) in this manner can reduce sensor errors close to zero since the interference of the power applied to the heater wire on the sensor wire signal is minimal. Further, changes to the voltage polarity applied to at least some sensors (e.g. thermistors) can cause a disturbance in readings. Essentially, it takes a little time for the signal to settle or stabilize and so preferably sensing occurs over a time period immediately preceding a zero crossing.

In some embodiments, a medical conduit, such as an inspiratory limb, is provided that comprises first and second segments. The two segments are preferably arranged and joined or connectable such that gases flow from a first end of the first segment, to a second end of the first segment, to a first end of the second segment and then to a second end of the second segment. According to such embodiments, a first heater wire part may be provided in the first segment and a second heater wire part may be provided in the second segment. The first and second heater wire parts may be configurable in a first mode in which only the first heater wire part is activated (i.e. generating heat) and in a second mode in which both the first and second heater wire parts are activated. Such arrangements, as discussed previously, can be desirable where a conduit conveys gases through different environments, such as to an infant inside an incubator from outside thereof. A diode, for example, may be provided intermediate the first and second heater wire parts such that when current of an AC supply flows in one direction, only the first heater wire part is powered and when the current flows in the other direction, both heater wire parts are powered. Other circuit/switching arrangements may be used. According to some embodiments, at least one sensor may be provided at or proximate a second end of the second segment i.e. at a patient-end of the conduit. For example, a thermistor may be provided to measure a temperature of gases flowing in the conduit. Sensor wires may be provided to facilitate reading of the sensor(s). According to some embodiments, the sensor and heater wires are connectable at or proximate to the first end of the first segment to the AC supply and/or a controller. Such a connection may conveniently be made via a cuff such as those described in PCT/NZ2013/000208. Where the segments are releasably connectable, similar cuff connectors may be used and reference is again made to PCT/NZ2013/000208. Similar to the previous embodiment, the sensor may be mounted to a circuit board at or proximate to the second end of the second segment, with heater and sensor wires joined thereto. Preferably, a waveform of the AC supply is monitored and/or known properties of the waveform are used to detect or determine the timing of one or more zero crossings (preferably falling zero crossings) of the AC supply waveform. According to such embodiments, the sensor(s) are preferably read at or about or after a zero crossing. Further, the sensor(s) are preferably read prior to the subsequent zero crossing of the same type. Reading of the sensor(s) may be repeated as desired, preferably with the zero crossing relationship maintained. Controlling reading of the sensor(s) in this manner can reduce sensor errors close to zero.

As will be apparent to one skilled in the art, the preferred controlled reading of sensors timed with respect to falling zero crossings may be applied to any embodiment described herein.

Embodiments further provide a controller for controlling reading of a sensor associated with a medical conduit, the controller being configured to read said sensor at or about or after a (preferably falling) zero crossing of an AC supply powering electrical circuitry of the medical conduit. Preferably, said reading is performed prior to the next falling zero crossing of said AC supply of the same type. Further features of the controller may be derived from the preceding statements.

Embodiments further provide a breathing assistance apparatus and/or a respiratory humidification system which is adapted to read a sensor at or about or after a (preferably falling) zero crossing of an associated AC power supply. Preferably, said reading is performed prior to the next zero crossing of said AC supply. Further features of the breathing assistance apparatus and/or respiratory humidification system may be derived from the preceding statements, and in fact said apparatus and/or system may include said conduits and/or said controller adapted to facilitate said controlled reading of the sensor or sensors.

Embodiments also provide corresponding methods.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

DETAILED DESCRIPTION

Figure 1:
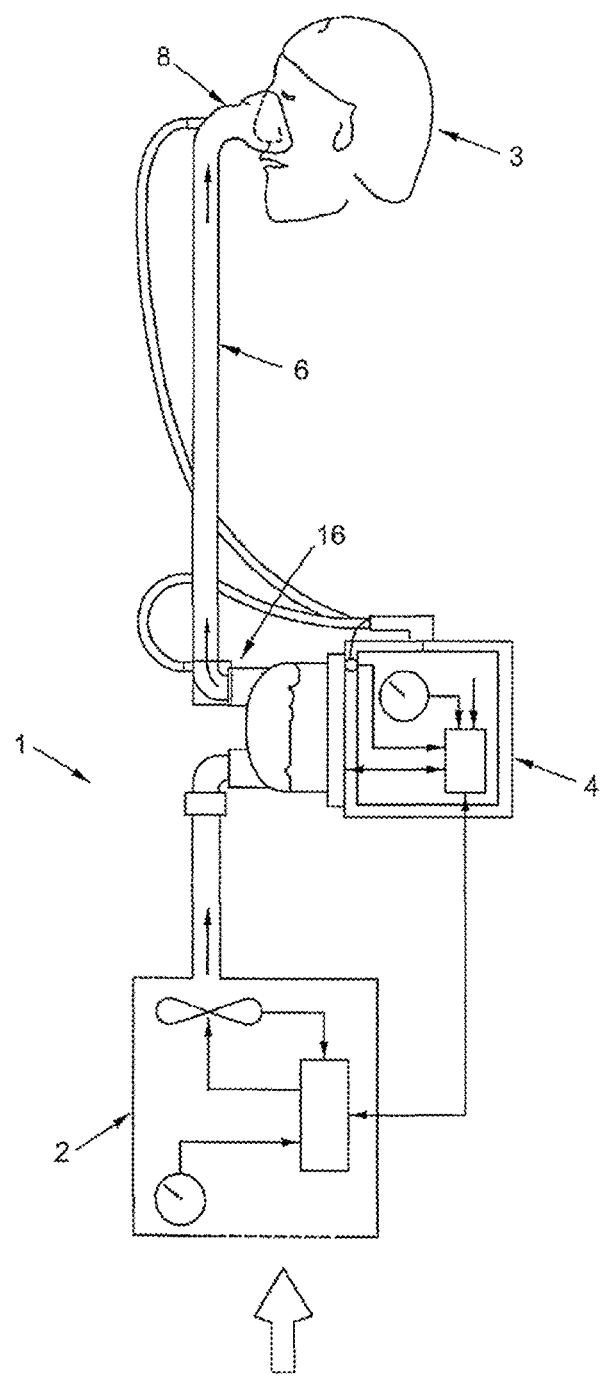
FIG. 1 is a schematic of a respiratory system to deliver respiratory gases to a patient.

Certain embodiments and examples of medical circuit components including inspiratory limbs, segmented inspiratory limbs and multiple-zone heating are described herein. Those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described herein.

The disclosure references heater wires, heating elements, and/or heaters in the context of providing heat to a conduit. Heater wire, for example, is a broad term and is to be given its ordinary and customary meaning to a person of ordinary skill in the art (that is, it is not to be limited to a special or customized meaning) and includes, without limitation, heater strips and/or conductive elements that produce heat when electrical power is provided. Examples of such heating elements include wires made of a conductive metal (e.g., copper), conductive polymers, conductive inks printed on a surface of a conduit, conductive materials used to create a track on a conduit, and the like. Furthermore, the disclosure references conduits, limbs, and medical tubes in the context of gas delivery. Tube, for example, is a broad term and is to be given its ordinary and customary meaning to a person of ordinary skill in the art and includes, without limitation, passageways having a variety of cross-sections such as cylindrical and non-cylindrical passageways. Certain embodiments may incorporate a composite tube, which may generally be defined as a tube comprising two or more portions, or, specifically, in some embodiments, two or more components, as described in greater detail below. The segmented limbs comprising the disclosed medical tubes can also be used in breathing circuits such as a continuous, variable, or bi-level positive airway pressure (PAP) system or other form of respiratory therapy. The terms conduit and limb should be construed in a manner that is similar to tube.

When a heated, humidified breathing tube is used for an incubator (or any region where there is a temperature change, such as around radiant warmers used for burn victims, or under a blanket used by a patient), the breathing tube will pass through at least two distinct zones: a lower temperature zone (such as the one outside the incubator) and a higher temperature zone (such as the one inside the incubator). If the tube is heated along its full length, one of the zones will tend to be at an undesirable, unsuitable, or non-optimal temperature, depending on which zone is sensed (e.g., which zone contains a temperature sensor). If the heater wire is controlled to a sensor inside the incubator (such as to a patient-end temperature sensor), the section outside the incubator will tend to be too cool, which can lead to condensation. Conversely, if the heater wire is controlled to a sensor outside the incubator, the section inside the incubator will tend to be too hot, which can lead to overheated gas being provided to the patient. Accordingly, some embodiments of the present disclosure describes systems and methods that provide for control over heat in a segmented breathing tube wherein each segment has an associated sensor providing feedback to a control module. Although several embodiments are described herein with respect to two zones, such a system could also be extended to apply to uses with additional zones, segments, or regions. For example, in an embodiment comprising three temperature zones, segments of the breathing tube may be heated based at least in part on three different temperature sensors in the zones. Furthermore, the embodiments disclosed herein can control the heat delivered to a breathing tube based on a parameter at the patient-end, bypassing or ignoring one or more of the sensors at intermediate points along the tube. Moreover, the embodiments disclosed herein can control the heat delivered to a breathing tube using parameters provided by sensors including, for example and without limitation, temperature sensors, humidity sensors, flow sensors, oxygen sensors, and the like. Other embodiments, while enabling different zones to be heated to different levels, may use fewer sensors. For example, according to one embodiment, two segments are provided and a single temperature sensor is associated with the breathing tube, preferably at or towards or near a patient-end of the tube. According to this embodiment, the segments may be configured such that only a first segment is heated or both segments are heated, wherein the first segment is preferably the segment most distal from the patient in terms of the gas flow path through the tube.

A control module can monitor and control the heating temperatures. The control module can be configured to provide heat to a first section of the breathing tube in a first mode and to the entire breathing tube in a second mode using embodiments of connector assemblies described herein. The control module may detect the presence of the first and/or second section of the breathing tube. To achieve this, the presence and/or absence of one or more sections of the breathing tube may be detected, with control of properties of the gases based at least in part modified accordingly. The embodiments described herein can be used without flying leads, exposed connectors, and/or patient-end electrical connections. Flying leads as used herein include electrical connections that extend externally of the breathing tubes, internally through the breathing tubes, and incorporated, molded, or otherwise formed or included as part of the breathing tubes. The control module can be located within the humidifier or externally to it. In some embodiments, the controller is located within the humidifier to control the heater wires associated with a first segment of an inspiratory limb, a second segment of an inspiratory limb, and an expiratory limb as well as read parameters from sensors associated with the first and second segments of the inspiratory limb and/or the expiratory limb.

The control module can also adaptively change the temperature for the segments. For example, the control module can monitor temperature sensors associated with one or more segments. The monitoring can be continuous, based on intervals, or other schemes such as interrupt or event-based monitoring. For example, the monitoring of temperature sensors can be based on reading values from an analog to digital converter, determining a voltage or current, sensing a logic condition, reading thermostatic devices, measuring thermistor values, measuring resistance temperature detectors, measuring the voltage of a thermocouple, or other methods for sensing temperature, including, but not limited to the use of semiconductor junction sensor, infrared or thermal radiation sensors, thermometers, indicators, or the like. In some embodiments, the temperature sensors are thermistors.

In some embodiments, the ratio of the power delivered to the first segment of the inspiratory limb and the second segment of the inspiratory limb can change during use based at least in part on feedback from sensor(s). For example, the ratio of power can be changed in a manner such that each segment is heated to a temperature to reduce or eliminate condensation. As a further example, the ratio of power can be changed so that overheated gas is not provided to the patient. In some embodiments, the ratio of power can be continuously changed based on feedback from sensor(s) (e.g., temperature sensors, humidity sensors, oxygen sensors, flow sensors, etc.). The ratio of power can be changed in different ways. For example, the ratio of power can be changed by altering the amplitude of a power signal (including, without limitation, the voltage and/or current), the duration of the power signal, the duty cycle of the power signal, or other suitable changes to the power signal. In an embodiment, the ratio of power is changed by altering the magnitude of the current provided.

Some embodiments provide for an inspiratory limb comprising heater wires that are not within the gas path, but are contained within a material that separates them from the gas path and that also insulates them from an external environment. In some embodiments, the circuitry used to provide power to heater wires and to read sensor(s) is internal to the inspiratory limb such that it is not exposed to the external environment. In some segmented tube embodiments, the heater wire is molded into the inspiratory or expiratory tube such that the ends of the heater wires in complementary segments of the tube contact an intermediate connector such that the heater wires electrically couple to the intermediate connector, wherein the intermediate connector can be configured to provide circuitry for heater wire control and/or sensor readings. In some embodiments, a duty cycle of a power source applied to a heater wire can be modified or varied to alter an amount of heat delivered to a gas as it flows along the associated segment.

Some embodiments described herein provide for a respiratory humidification system that is configured to deliver warm, humidified gas to a patient or other user. The gas is passed through a liquid chamber which is filled with a liquid (e.g., water) that is heated using a heater plate. The liquid evaporates in the chamber and combines with the gas which flows over it, thereby heating and/or humidifying the gas. The humidified gas can be directed to an inspiratory limb having one or more heater wires associated therewith. The heater wires can be selectively powered to provide a defined, desired, appropriate, or selected amount of heat to the humidified gas. In some embodiments, the respiratory humidification system can be used in conjunction with an incubator or radiant warmer. The inspiratory limb can be segmented such that a first segment is outside the incubator and a second segment is inside the incubator. Furthermore, a first set of heater wires can be associated with the first segment and a second set of heater wires can be associated with the second segment. The humidification system can be configured to provide power to the first set of heater wires in a first mode and to the first set and second set of heater wires in a second mode. In some embodiments, the humidification system can be configured to provide power to the first set of heater wires in a first mode and to the second set of heater wires in a second mode. The inspiratory limb can include sensors at the end of each segment or one segment to provide feedback to the humidification system for use in selecting a power to deliver to the sets of heater wires in the segments. In some embodiments, the humidification system can include an expiratory limb having associated heater wires which are also selectively controlled by the humidification system. In this application, the segmented limb is described with reference to an inspiratory limb. However, the described features can be applied to an expiratory limb, as well as other medical tubes.

Respiratory Humidification Systems

FIG. 1 shows a respiratory system 1 which can include, but is not limited to, the following components: a pressurized gases source 2, such as a blower or ventilator, adapted to generate a supply of gases to be delivered to a patient 3; a humidification device 4 adapted to condition the supply of gases; a medical tube 6 adapted to deliver the gases to a patient interface 8, which then delivers the gases to the patient 3; and a connector 16 adapted to connect the medical tube 6 to the humidification device 4.

The patient interface 8 as described herein may refer to a mask, nasal mask, nasal prongs, oral mask, tracheal mask, or nasal pillows.

The humidification device 4 as described herein may refer to any device that conditions gases. This may include heating the gases and/or humidifying the gases.

Gases as described herein may refer to air, oxygen, carbon dioxide, or a mixture of any such gases, or a combination of any such gases with one or more medicaments or aerosols that may be delivered to the patient 3 via the patient interface 8.

The medical tube 6 as described herein may refer to a tube, conduit, circuit, or hose. The medical tube 6 may comprise one or more wires. The one or more wires may comprise at least one heater wire, at least one sensor wire, and/or any other type of electrical conductor. The one or more wires may be within the medical tube 6. The one or more wires may be lying along an inner or outer surface of the medical tube 6. The one or more wires may be spirally wound onto the medical tube 6 or into the medical tube 6 such that the one or more wires may be embedded in the wall of the medical tube 6.

The medical tube 6 is preferably heated. The medical tube 6 may include insulation to reduce condensate from forming within the medical tube 6. Condensate may form if heated, humidified gases within the medical tube 6 cool down during transit. To reduce or eliminate condensate formation, the medical tube 6 may be heated. This heating may be provided by the one or more wires comprising one or more heater wires.

A terminating portion of the medical tube 6 may be provided to terminate the one or more wires at a connector 16 such that an electrical connection may be formed between the medical tube 6 and a component of the respiratory system 1. The connector 16 may provide a pneumatic connection between the medical tube 6 and a component of the respiratory system 1. A component of the respiratory system 1 as described herein may refer to a patient interface or a humidification device. The connector 16 may provide either one of or both an electrical and pneumatic connection between the medical tube 6 and a component of the respiratory system 1.

The one or more wires may also comprise one or more sensing wires. The one or more sensing wires may be used to sense gases properties such as temperature, flow, humidity, or pressure. In some embodiments, the one or more sensing wires may be used to sense temperature. In some embodiments, the one or more sensing wires may be connected to one or more sensors that may be used to sense one or more of these gases properties.

Figure 2:
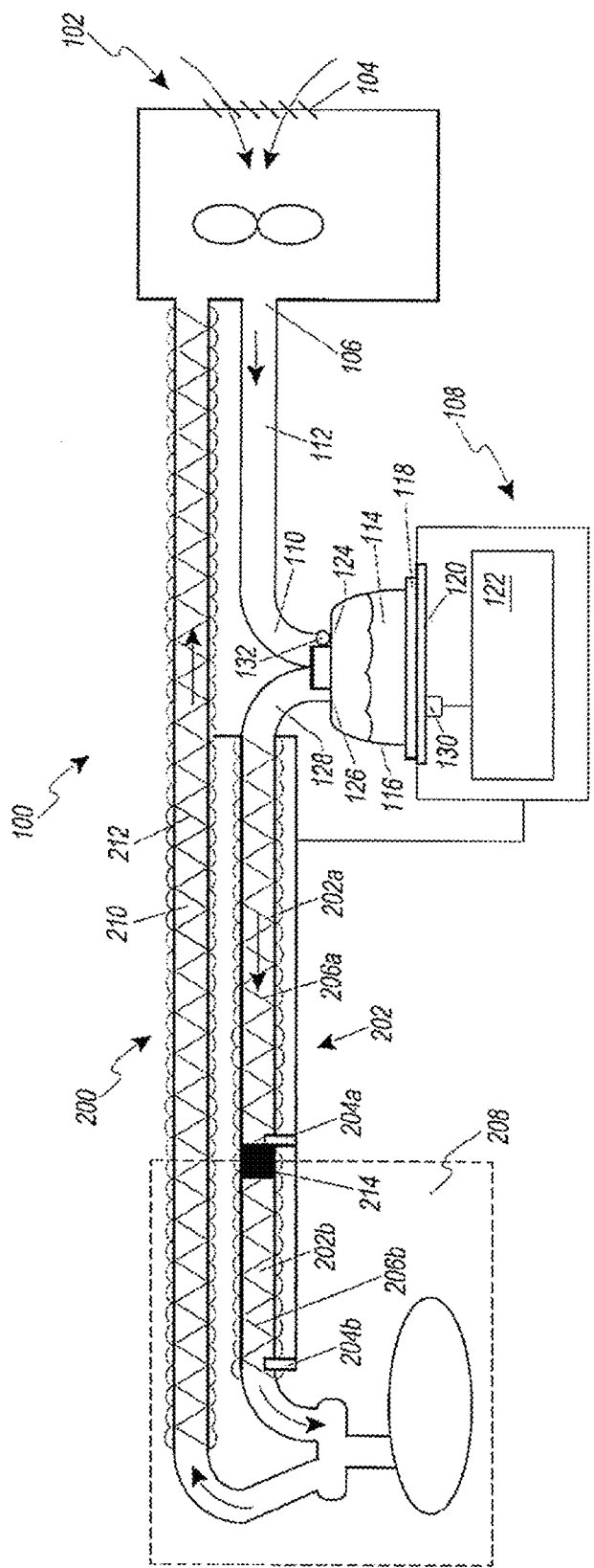
FIG. 2 illustrates an example respiratory humidification system for delivering humidified gas to a user, the respiratory humidification system having a breathing circuit that includes a segmented inspiratory limb with sensors in each segment.

FIG. 2 illustrates another example respiratory humidification system 100 for delivering humidified gas to a user, the respiratory humidification system 100 having a breathing circuit 200 that includes a segmented inspiratory limb 202 with sensors 204a, 204b in each segment. The segmented inspiratory limb 202 can be used in conjunction with an incubator 208, as illustrated, or with another system where there are different temperatures along different segments of the inspiratory limb 202, such as in conjunction with a radiant warmer. The segmented inspiratory limb 202 can be used to provide different levels of heat to different segments of the inspiratory limb 202a, 202b to reduce or prevent condensation and/or to control a temperature of gas delivered to a user.

The respiratory humidification system 100 comprises a pressurized gas source 102. In some implementations, the pressurized gas source 102 comprises a fan, blower, or the like. In some implementations, the pressurized gas source 102 comprises a ventilator or other positive pressure generating device. The pressurized gas source 102 comprises an inlet 104 and an outlet 106.

The pressurized gas source 102 provides a flow of fluid (e.g., oxygen, anesthetic gases, air or the like) to a humidification unit 108. The fluid flow passes from the outlet 106 of the pressurized gas source 102 to an inlet 110 of the humidification unit 108. In the illustrated configuration, the humidification unit 108 is shown separate of the pressurized gas source 102 with the inlet 110 of the humidification unit 108 connected to the outlet 106 of the pressurized gas source 102 with a conduit 112. In some implementations, the pressurized gas source 102 and the humidification unit 108 can be integrated into a single housing.

While other types of humidification units can be used with certain features, aspects, and advantages described in the present disclosure, the illustrated humidification unit 108 is a pass-over humidifier that comprises a humidification chamber 114 and an inlet 110 to the humidification chamber 114. In some implementations, the humidification chamber 114 comprises a body 116 having a base 118 attached thereto. A compartment can be defined within the humidification chamber 116 that is adapted to hold a volume of liquid that can be heated by heat conducted or provided through the base 118. In some implementations, the base 118 is adapted to contact a heater plate 120. The heater plate 120 can be controlled through a controller 122 or other suitable component such that the heat transferred into the liquid can be varied and controlled.

The controller 122 of the humidification unit 108 can control operation of various components of the respiratory humidification system 100. While the illustrated system is illustrated as using a single controller 122, multiple controllers can be used in other configurations. The multiple controllers can communicate or can provide separate functions and, therefore, the controllers need not communicate. In some implementations, the controller 122 may comprise a microprocessor, a processor, or logic circuitry with associated memory or storage that contains software code for a computer program. In such implementations, the controller 122 can control operation of the respiratory humidification system 100 in accordance with instructions, such as contained within the computer program, and also in response to internal or external inputs. The controller 122, or at least one of the multiple controllers, can be located with the breathing circuit, either attached to the breathing circuit or integrated as part of the breathing circuit.

The body 116 of the humidification chamber 114 comprises a port 124 that defines the inlet 110, and a port 126 that defines an outlet 128 of the humidification chamber 114. As liquid contained within the humidification chamber 114 is heated, liquid vapor is mixed with gases introduced into the humidification chamber 114 through the inlet port 124. The mixture of gases and vapor exits the humidification chamber 114 through the outlet port 126.

The respiratory humidification system 100 includes a breathing circuit 200 comprising the inspiratory limb 202 connected to the outlet 128 that defines the outlet port 126 of the humidification unit 108. The inspiratory limb 202 conveys toward a user the mixture of gases and water vapor that exits the humidification chamber 114. The inspiratory limb 202 can include a heating element 206 positioned along the inspiratory limb 202, wherein the heating element 206 is configured to reduce condensation along the inspiratory limb 202, to control a temperature of gas arriving at the user, to maintain humidity of the gas, or any combination of these. The heating element 206 can raise or maintain the temperature of the gases and water vapor mixture being conveyed by the inspiratory limb 202. In some implementations, the heating element 206 can be a wire that defines a resistance heater. By increasing or maintaining the temperature of the gases and water vapor mixture leaving the humidification chamber 114, the water vapor is less likely to condensate out of the mixture.

The respiratory humidification system 100 can be used in conjunction with an incubator 208. The incubator 208 can be configured to maintain a desired environment for a user within the incubator 208, such as a selected, defined, or desired temperature. Within the incubator 208, therefore, an interior ambient temperature may be different than a temperature outside the incubator 208. Thus, the incubator 208 causes, defines, creates, or maintains different temperature zones along the inspiratory limb 202, where the interior temperature is typically hotter than the exterior temperature. Having at least two different temperature zones along the inspiratory limb 202 can create problems during delivery of gas to a user such as condensation along the inspiratory limb 202, delivering a gas that has a temperature that is too high, or both.

The respiratory humidification system 100 can include an expiratory limb 210 with associated heating element 212. In some embodiments, the expiratory limb 210 and the inspiratory limb 202 can be connected using a suitable fitting (e.g., a wye-piece). In some embodiments, the respiratory humidification system 100 can be used in conjunction with a radiant warmer, under a blanket, or in other systems or situations that create two or more temperature zones. The systems and methods described herein can be used with such systems and are not limited to implementations incorporating incubators.

The inspiratory limb 202 can be divided into segments 202a and 202b where a first segment 202a can be a portion of the inspiratory limb 202 that is outside the incubator 208 and a second segment 202b (e.g., an incubator extension), can be a portion of the inspiratory limb 202 that is inside the incubator 208. The first and second segments 202a, 202b can be different lengths or the same length. In some embodiments, the second segment 202b can be shorter than the first segment 202a, and, in certain implementations, the second segment 202b can be about half as long as the first segment 202a. The first segment 202a, for example, can have a length that is at least about 0.5 m and/or less than or equal to about 2 m, at least about 0.7 m and/or less than or equal to about 1.8 m, at least about 0.9 m and/or less than or equal to about 1.5 m, or at least about 1 m and/or less than or equal to about 1.2 m. The second segment 202b, for example, can have a length that is at least about 0.2 m and/or less than or equal to about 1.5 m, at least about 0.3 m and/or less than or equal to about 1 m, at least about 0.4 m and/or less than or equal to about 0.8 m, or at least about 0.5 m and/or less than or equal to about 0.7 m.

The segments of the inspiratory limb 202a, 202b can be coupled to one another to form a single conduit for gas delivery. In some embodiments, the first segment 202a can include one or more first heater wires 206a and one or more first sensors 204a and can be used without the second segment 202b. The controller 122 can be configured to control the first heater wires 206a and read the first sensor 204a without the second segment 202b being coupled to the first segment 202a. Furthermore, when the second segment 202b is coupled to the first segment 202a, the controller 122 can be configured to control the first and second heater wires 206a, 206b and read the first and second sensors 204a, 204b in their respective segments. In some embodiments, the controller 122 can be configured to control the respective first and second heater wires 206a, 206b and to read the respective first and second sensors 204a, 204b when the second segment 202b is attached; and to control the first heater wires 206a and to read the first sensor 204a when the second segment 202b is not attached, without modification to the controller 122 or humidification unit 108. Thus, the same controller 122 and/or humidification unit 108 can be used whether the inspiratory limb 202 includes both the first and second segments 202a, 202b or only the first segment 202a. In some embodiments, the controller 122 can be further configured to control the heater wires 212 in the expiratory limb 210 without modification to the controller 122 or humidification unit 108. Accordingly, the respiratory humidification system 100 can function with or without the second segment 202b attached and/or with or without the expiratory limb 210 attached.

In some embodiments, the first and second segments 202a, 202b are permanently joined together to form a single conduit for gas delivery. As used here, permanently joined can mean that the segments 202a, 202b are joined together in a manner that makes it difficult to separate the segments, such as through the use of adhesives, friction fits, overmolding, mechanical connectors, and the like. In some embodiments, the first and second segments 202a, 202b are configured to be releasably coupled. For example, the first segment 202a can be used for gas delivery without the second segment 202b, or the first and second segments 202a, 202b can be coupled together to form a single conduit for gas delivery. In some embodiments, the first and second segments 202a, 202b can be configured such that they can be coupled together in only one configuration. For example, the first segment 202a can have a defined chamber-end (e.g., an end closest to the chamber 114 or humidification unit 108 along a direction of the flow of the humidified gas to the patient) and a defined patient-end (e.g., an end closest to the patient along a direction of the flow of the humidified gas to the patient) wherein the chamber-end is configured to couple to components at the chamber 114 and/or humidification unit 108. The second segment 202b can have a defined chamber-end and a defined-patient end wherein the chamber-end is configured to only couple to the patient-end of the first segment 202a. The chamber-end of the first segment 202a can be configured to not couple with either end of the second segment 202b. Similarly, the patient-end of the first segment 202a can be configured to not couple with the patient-end of the second segment 202b. Similarly, the patient-end of the second segment 202b can be configured to not couple with either end of the first segment 202a. Accordingly, the first and second segments 202a, 202b can be configured to be coupled in only one way to form a single conduit for gas delivery. In some embodiments, the first and second segments 202a, 202b can be configured to be coupled in a variety of configurations. For example, the first and second segments 202a, 202b can be configured to not include a defined patient-end and/or a defined chamber-end. As another example, the first and second segments 202a, 202b can be configured such that the patient-end and/or the chamber-end of the first segment 202a can couple to either the chamber-end or the patient-end of the second segment 202b. Similarly, the first and second segments 202a, 202b can be configured such that the chamber-end and/or the patient-end of the second segment 202a can couple to either the chamber-end or the patient-end of the second segment 202b.

The respiratory humidification system 100 can include an intermediate connector 214 that can be configured to electrically couple elements of the first and second segments 202a, 202b of the inspiratory limb 202. The intermediate connector 214 can be configured to electrically couple the heater wires 206a in the first segment 202a to the heater wires 206b in the second segment 202b to enable control of the heater wires 206a, 206b using the controller 122. The intermediate connector 214 can be configured to electrically couple the second sensor 204b in the second segment 202b to the first sensor 204a in the first segment to enable the controller 122 to acquire their respective outputs. The intermediate connector 214 can include electrical components that enable selective control of the heater wires 206a, 206b and/or selective reading of the sensors 204a, 204b. For example, the intermediate connector 214 can include electrical components that direct power through the first heater wires 206a in a first mode and through the first and second heater wires 206a, 206b in a second mode. The electrical components included on the intermediate connector 214 can include, for example and without limitation, resistors, diodes, transistors, relays, rectifiers, switches, capacitors, inductors, integrated circuits, micro-controllers, micro-processors, RFID chips, wireless communication sensors, and the like. In some embodiments, the intermediate connector 214 can be configured to be internal to the inspiratory limb 202 such that it is substantially shielded from external elements (e.g., less than 1% of the water, particulates, contaminates, etc. from an environment external to the inspiratory limb 202 contacts the intermediate connector 214). In some embodiments, some of the electrical components on the intermediate connector 214 can be configured to be physically isolated from the humidified gas within the inspiratory limb 202 to reduce or prevent damage that may result from exposure to humidity. In some embodiments, the intermediate connector 214 can include relatively inexpensive passive electrical components to reduce cost and/or increase reliability.

The inspiratory limb 202 can include sensors 204a, 204b in respective segments of the inspiratory limb 202a, 202b. The first sensor 204a can be positioned near an end of the first segment 202a, close to the incubator 208 so that the parameter derived from the first sensor 204a corresponds to a parameter of the humidified gas entering the second segment 202b. The second sensor 204b can be positioned near an end of the second segment 202b so that the parameter derived from the second sensor 204b corresponds to a parameter of the humidified gas delivered to the patient or user. The output of the sensors 204a, 204b can be sent to the controller 122 as feedback for use in controlling power delivered to the heating elements 206a, 206b of the segments of the inspiratory limb 202a, 202b. In some embodiments, one or both of the sensors 204a, 204b can be temperature sensors, humidity sensors, oxygen sensors, flow sensors, or the like. A temperature sensor can be any suitable type of temperature sensor including, for example and without limitation, a thermistor, thermocouple, digital temperature sensor, transistor, and the like. The parameters provided by or derived from the sensors can include, for example and without limitation, temperature, humidity, oxygen content, flow rate, or any combination of these or the like.

The controller 122 can be configured to control the heater wires 206a and 206b, to receive feedback from the sensors 204a and 204b, to provide logic to control power to the heater wires 206a and 206b, to adjust control of the heater wires 206a and 206b in response to readings from the sensors 204a and 204b, to detect a presence of a second segment 202b of the inspiratory limb 202 (for example, the second segment 202b may have an identification element associated therewith such as a dedicated resistor or other element specifically or predominantly used for identification purposes or an inherent characteristic of the second segment may be used, such as a thermistor have a resistance within a predetermined range), to derive parameters from the readings from the sensors 204a and 204b, and the like. In some embodiments, the controller 122 includes a power source configured to deliver electrical power to the heater wires. The power source can be a source of alternating current or direct current. In some embodiments, the controller 122 can receive input from a heater plate sensor 130. The heater plate sensor 130 can provide the controller 122 with information regarding a temperature and/or power usage of the heater plate 120. In some embodiments, the controller 122 can receive input from a flow sensor 132. Any suitable flow sensor 132 can be used and the flow sensor 132 can be positioned between ambient air and the humidification chamber 114 or between the pressurized gas source 102 and the humidification chamber 114. In the illustrated system, the flow sensor 132 is positioned on the inlet port 124 of the humidification chamber 114.

Detection of the presence of the second segment may be used to alter the control of the apparatus. For example, control algorithms adapted for providing humidified gases to an infant inside an incubator may be used. Thus, applicable temperature profiles and/or values and/or ranges may be used and flow and/or pressures of the gases delivered may be adjusted.

Breathing Circuit Hardware Configurations

Figure 3:
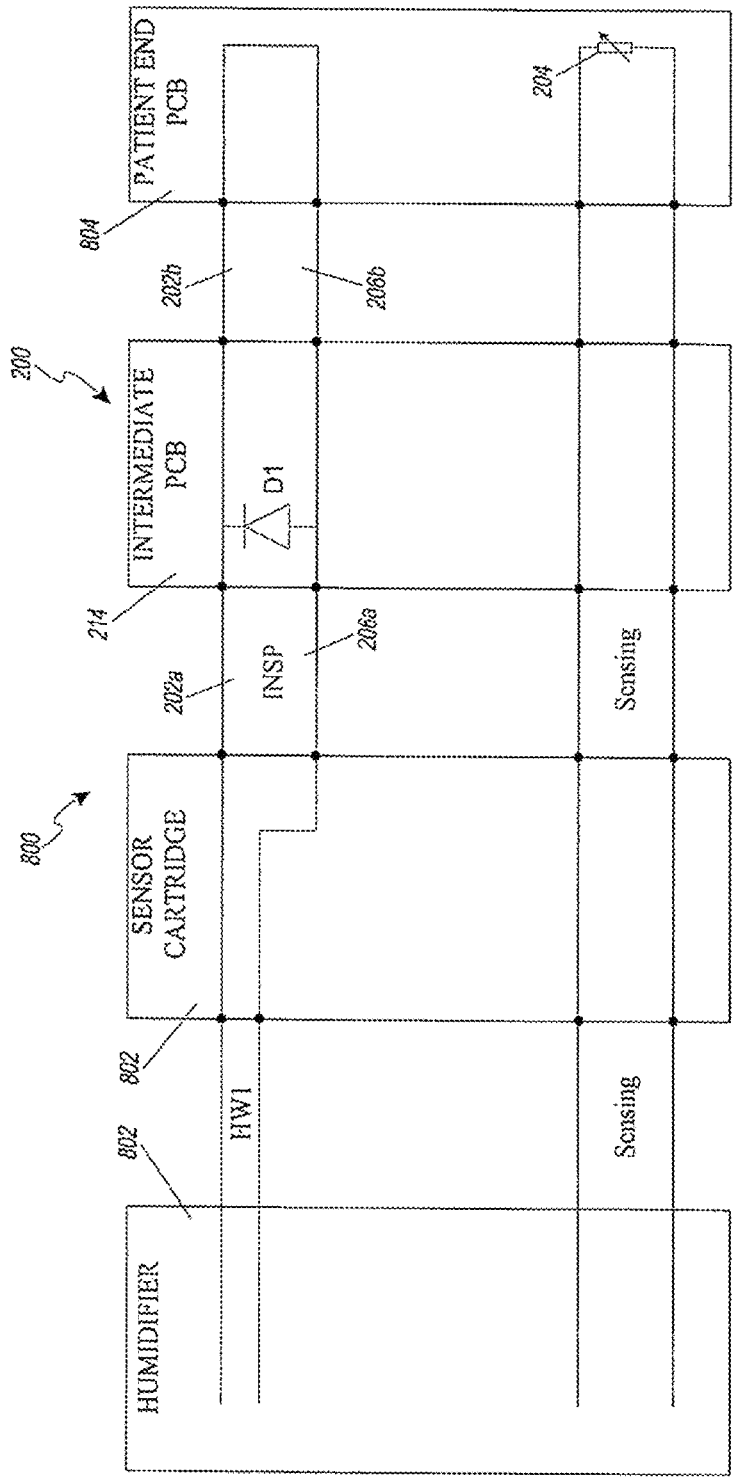
FIG. 3 illustrates an example hardware configuration for a breathing circuit with an inspiratory limb having a first and a second segment.

FIG. 3 illustrates an example diagram of a hardware configuration 800 for a breathing circuit 200 having a first segment 202a of an inspiratory limb, a second segment 202b of the inspiratory limb, and may include an expiratory limb (not shown) or exhaled gases may be vented to the atmosphere. The hardware configuration 800 can include a humidifier 108 configured to couple the wiring of the heater wires HW1, and the wiring for sensor 204. In some embodiments, the sensor cartridge 802 can be configured to couple the wiring of the heater wires HW1 and the wiring for sensor 204. The heater wires HW1 can be controlled in two modes. In a first mode, the first heater wires 206a receive electrical power while the second heater wires 206b do not. In a second mode, the first and second heater wires 206a, 206b receive electrical power.

The hardware configuration 800 can include an intermediate printed circuit board (PCB) 214 that includes a power diode D1 The intermediate PCB 214 can include heat pads to dissipate heat generated by the diode D1 to reduce the effects on the sensor 204. The hardware configuration 800 can include a patient-end PCB 804 having two heater wires and a sensor 204, wherein the heater wires 206b are directly electrically coupled. In the first mode of operation, electrical power can be provided to HW1 such that current flows through heater wires 206a and through diode D1 while substantially no current flows through heater wires 206b (e.g., less than 1% of the current through heater wires 206a flows through heater wires 206b). In the second mode of operation, electrical power can be provided to HW1 such that current flows through heater wires 206a and 206b. The first and second modes of operation can be controlled at least in part by the direction of the current flow through the heater wires HW1.

In some embodiments, the sensor cartridge 802 can be located within the humidification system 100 or external to the system.

Figure 4:
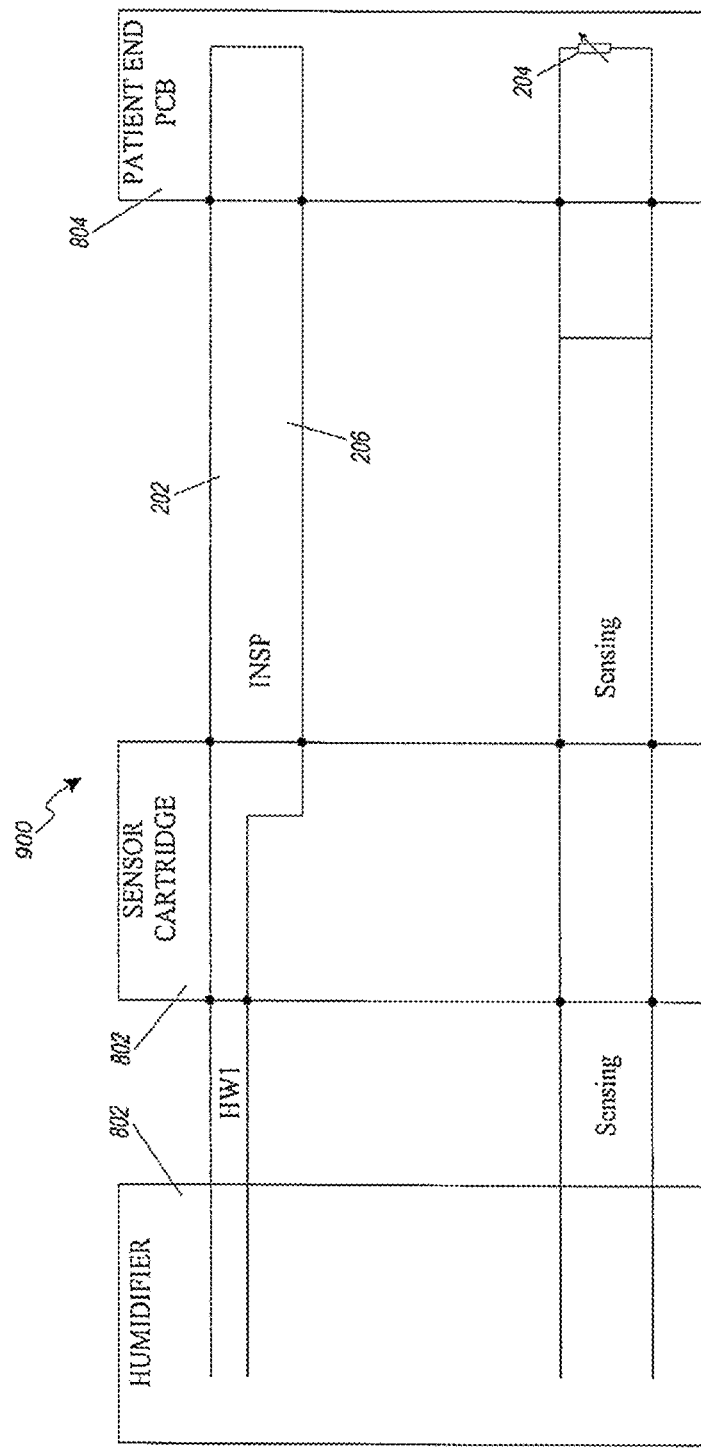
FIG. 4 illustrates an example hardware configuration for a breathing circuit with an inspiratory limb.

FIG. 4 illustrates an example diagram of a hardware configuration 900 for an inspiratory limb 6 of a respiratory system 1 that may include an expiratory limb (not shown) or exhaled gases may be vented to the atmosphere. The hardware configuration 900 can include a humidifier 4 configured to couple the wiring of the heater wires HW1, and the wiring for sensor 204. In some embodiments, the sensor cartridge 802 can be configured to couple the wiring of the heater wires HW1 and the wiring for sensor 204.

The hardware configuration 900 can include a patient-end PCB 804 having two heater wires and a sensor 204, wherein the heater wires 206 are directly electrically coupled. Electrical power can be provided to HW1 such that current flows through heater wires 206 and generate heat.

Other configurations, including embodiments in which an expiratory limb is heated and/or where one or more additional sensors are provided, can be derived without invention from PCT/NZ2013/00208 but implementing the novel sensor reading control disclosed herein.

Embodiments of the systems shown in FIGS. 1-4 may include a sinusoidal pulse width modulation (SPWM) driver that provides for turning a heater plate and heater wires ON or OFF, the heater plate for heating the contents of a humidification chamber and the heater wires being, for example, the heater wires HW1 of an inspiratory conduit. The driver may supply, for example, two 100-bit patterns, one for the heater plate and one for the heater wire. Each bit in a bit pattern may cause the SPWM driver to switch the respective heater ON or OFF. Switching may be done at each falling zero crossing of the mains voltage to reduce the stress on the power supply that would be caused by an abrupt transition from zero power to the maximum power level. The choice of falling edge or rising edge is somewhat arbitrary, what is important is that the switch occurs at the zero crossing and only every full AC cycle. Thus, the heaters can be switched ON or OFF 50 times per second (every 20 ms) or 60 times per second (every 16.67 ms) for 50 Hz mains and 60 Hz mains, respectively. This is useful because the sensor, e.g. a patient-end thermistor, measurement cycle can be aligned with the mains cycle, the mains and heater wire cycles already being aligned.

Figure 5:
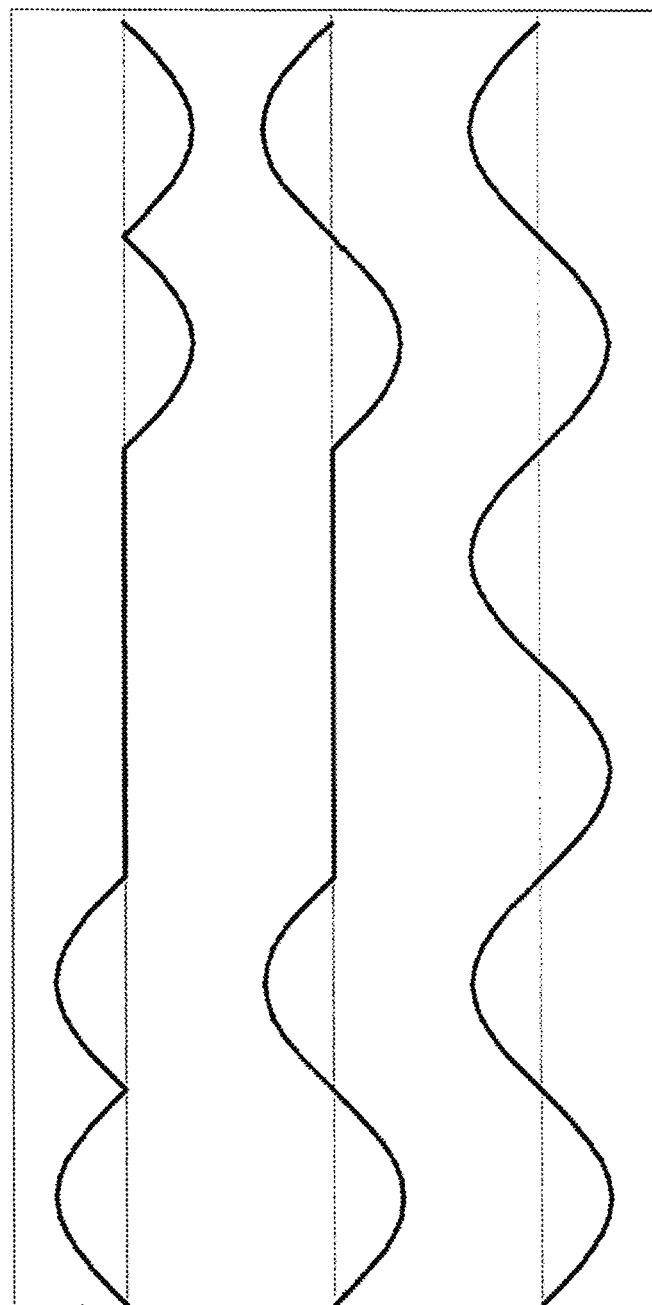
FIG. 5 is a chart showing the relationship between the mains AC cycle and the heater wire cycles of the heater wires depicted in FIGS. 3 and 4.

FIG. 5 is a chart showing the relationship between the mains AC cycle and the heater wire cycles of the heater wires depicted in FIGS. 3 and 4.

Figure 6:
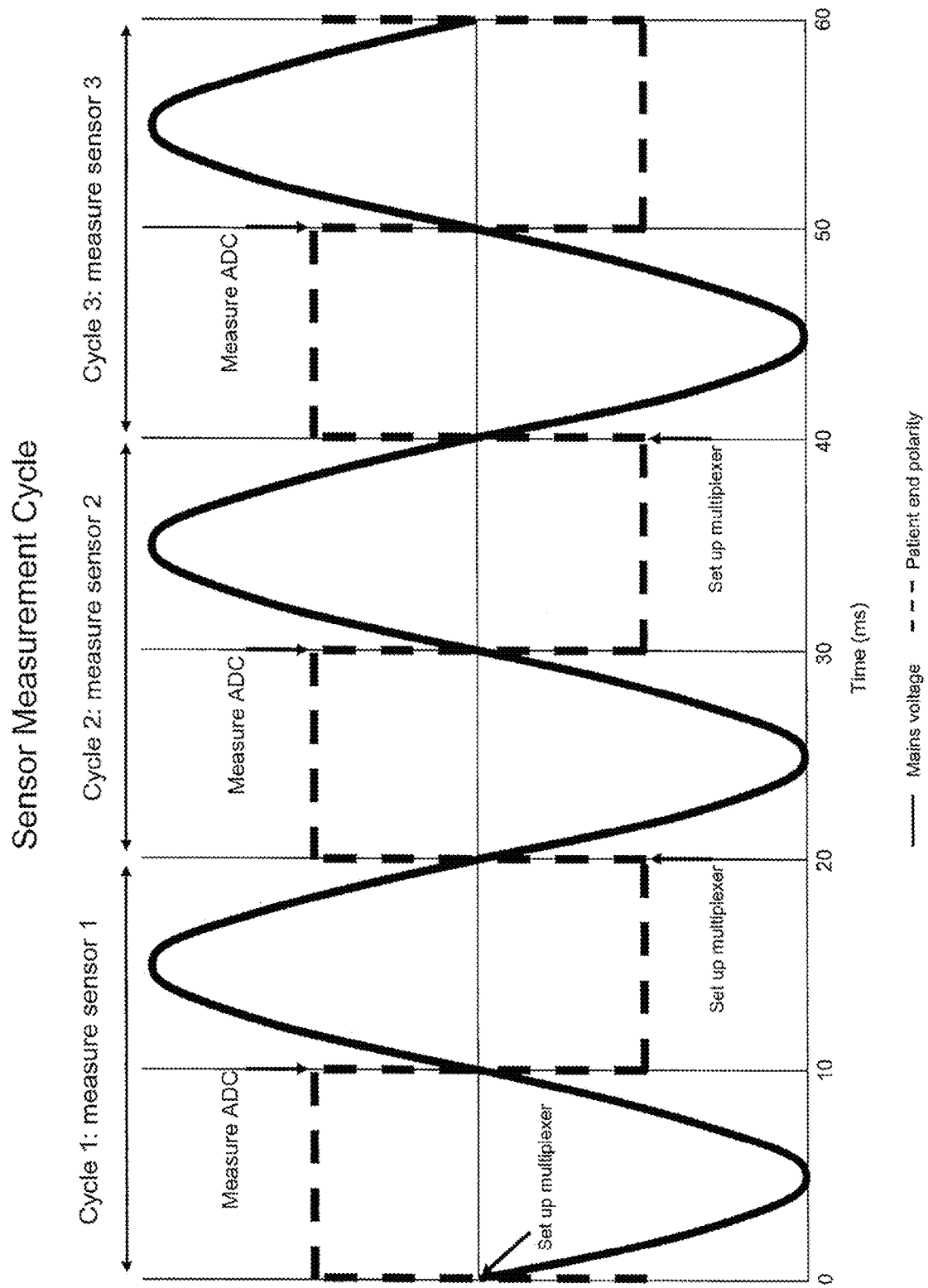
FIG. 6 is a chart depicting measurement of sensors with respect to the mains voltage waveform.

FIG. 6 is a chart depicting measurement of sensors with respect to the mains voltage waveform. When the falling zero crossing occurs on the mains cycle, various setup steps may be taken to prepare for the sensor reading, including switching the polarity on the sensing wire to positive. As the rising zero occurs on the mains cycle, the measurement is taken and the polarity on the sensing wire is reversed. The falling zero crossing and frequency may be detected by analyzing the mains voltage with the rising zero crossing being predicted.

CONCLUSION

Examples of respiratory humidification systems with sensor reading control and associated components and methods have been described with reference to the figures. The figures show various systems and modules and connections between them. The various modules and systems can be combined in various configurations and connections between the various modules and systems can represent physical or logical links. The representations in the figures have been presented to clearly illustrate principles related to providing sensor reading control, and details regarding divisions of modules or systems have been provided for ease of description rather than attempting to delineate separate physical embodiments. The examples and figures are intended to illustrate and not to limit the scope of the inventions described herein. For example, the principles herein may be applied to a respiratory humidifier as well as other types of humidification systems, including surgical humidifiers. The principles herein may be applied in respiratory applications as well as in other scenarios where a temperature of gases is to be controlled along multiple segments subject to varying ambient temperatures.

As used herein, the term "processor" refers broadly to any suitable device, logical block, module, circuit, or combination of elements for executing instructions. For example, controllers, as referred to herein, can include any conventional general purpose single- or multi-chip microprocessor such as a Pentium® processor, a MIPS® processor, a Power PC® processor, AMD® processor, ARM® processor, or an ALPHA® processor. In addition, controllers can include any conventional special purpose microprocessor such as a digital signal processor or a microcontroller. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein, or can be a pure software in the main processor. For example, logic module 504 can be a software-implemented function block which does not utilize any additional and/or specialized hardware elements. Controllers can be implemented as a combination of computing devices, e.g., a combination of a DSP and a microprocessor, a combination of a microcontroller and a microprocessor, a plurality of microprocessors, one or more microprocessors in conjunction with a DSP core, or any other such configuration.

Data storage can refer to electronic circuitry that allows data to be stored and retrieved by a processor. Data storage can refer to external devices or systems, for example, disk drives or solid state drives. Data storage can also refer to fast semiconductor storage (chips), for example, Random Access Memory (RAM) or various forms of Read Only Memory (ROM), which are directly connected to a communication bus or controller. Other types of data storage include bubble memory and core memory. Data storage can be physical hardware configured to store data in a non-transitory medium.

Although certain embodiments and examples are disclosed herein, inventive subject matter extends beyond the specifically disclosed embodiments to other alternative embodiments and/or uses, and to modifications and equivalents thereof. Thus, the scope of the claims or embodiments appended hereto is not limited by any of the particular embodiments described herein. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z each to be present. As used herein, the words "about" or "approximately" can mean a value is within +10%, within +5%, or within ±1% of the stated value.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A controller for a breathing assistance apparatus, the breathing assistance apparatus comprising a conduit for conveying gases therein, the conduit comprising first and second segments that are integral or connectable to provide an extended conduit, the conduit further comprising circuitry, wherein the circuitry comprises at least one heater wire part configured to heat the gases in the conduit, in use, and at least one sensor wire part comprising at least one sensor configured to monitor a parameter of the gases in the conduit, in use, the controller being configured to:
    receive a signal indicative of a presence or absence of one or both the first segment or the second segment so as to implement control dependent on which segment(s) is/are determined to be present or absent;
    control application of an AC power waveform to the at least one heater wire part; and
    control selective reading of the at least one sensor, wherein the controller is configured to read the at least one sensor at or about a particular portion of the AC power waveform provided to the at least one heater wire part.

2. The controller of claim 1, wherein said particular portion of the AC power waveform commences at or about or after a first zero crossing of the AC power waveform, and terminates at or before a second, subsequent zero crossing of the AC power waveform, the first zero crossing and the second, subsequent zero crossing being consecutive zero crossings of a same type, wherein types of zero crossings include a rising zero crossing and a falling zero crossing.

3. The controller of claim 2, wherein the first zero crossing is a falling zero crossing.

4. The controller of claim 1, wherein the at least one sensor comprises two or more sensors, at least one of the two or more sensors located in the first segment and at least another one of the two or more sensors located in the second segment, the controller being configured to receive sensed readings from each of said two or more sensors.

5. The controller of claim 4, wherein the controller is further configured to:
    control reading of a first of said two or more sensors commencing at or about or after a first particular portion of the AC power waveform, and control reading of a second of said two or more sensors commencing at a second particular portion of the AC power waveform,
wherein the first and second particular portions are consecutive particular portions.

6. A breathing assistance apparatus comprising:
a pressurized gas source to provide a flow of fluid;
a humidification unit to humidify the fluid, in use, the humidification unit comprising the controller as claimed in claim 4; and
an outlet connectable to the conduit for conveying gases therein, the conduit comprising:
the first and second segments that are integral, or connectable together, to provide the extended conduit, the first and second segments each having the at least one or another one of the two or more sensors for monitoring the parameter of the gases in the conduit, in use, and
the circuitry comprising the at least one heater wire part to heat gases in the conduit.

7. The controller of claim 1, wherein:
in response to determining that only the first segment is present, the controller adopts a first mode, the first mode adapted for adult users and/or applications in which surrounding environmental conditions are substantially the same along a length of the conduit; or
in response to determining that the first and second segments are both present, the controller adopts a second mode, the second mode adapted for incubators and/or applications in which the surrounding environmental conditions are variable along the length of the conduit.

8. The controller of claim 7, wherein the controller is further configured to switch between the first mode and the second mode dependent, at least in part, on the selective reading of the at least one sensor.

9. The controller of claim 1, wherein the controller is further configured to control the application of the AC power waveform to the at least one heater wire part such that:
the AC power waveform applied to the at least one heater wire part transitions from flat to a negative half of a full cycle, and/or
the AC power waveform applied to the at least one heater wire part transitions from a positive half of the full cycle to flat.

10. The controller of claim 1, wherein said at least one heater wire part comprises first and second heater wire parts, the first segment comprising the first heater wire part and the second segment comprising the second heater wire part, wherein, in response to determining that the first segment and the second segment are both present, the controller is configured to:
control selective application of the AC power waveform during a first time period to the first heater wire part only, and
control selective application of the AC power waveform in a second time period to both the first and second heater wire parts or to the second heater wire part only.

11. The controller of claim 10, wherein the controller is further adapted to control the application of the AC power waveform:
to the first said heater wire part such that the AC power waveform transitions:
from flat to a first of two positive half cycles; and/or
to flat following the two positive half cycles, or
to the second said heater wire part such that the AC power waveform transitions:
from flat or off to a first of two negative half cycles; and/or
to flat following the two negative half cycles, or
to both the first and second said heater wire parts such that the AC power waveform transitions:
from flat or off to the first of the two negative half cycles; and/or
to flat following the two negative half cycles.

12. The controller of claim 1, wherein the breathing assistance apparatus comprises an inspiratory limb, the inspiratory limb comprising the first and second segments and the at least one heater wire part including a first heater wire part and a second heater wire part, the breathing assistance apparatus further comprising an expiratory limb, the expiratory limb comprising a third segment, wherein the third segment comprises at least one third heater wire part to heat the gases in the expiratory limb, the controller being configured to control the application of the AC power waveform to the at least one third heater wire part:
independent of heating of the first and second heater wire parts;
in parallel with the first heater wire part; and/or
in parallel with the first and second heater wire parts.

13. The controller of claim 1, wherein at least a portion of said at least one sensor wire part is positioned adjacent at least a corresponding portion of said at least one heater wire part.

14. The controller of claim 1, wherein the second segment comprises an identification element, wherein the signal received by the controller is dependent on the identification element.

15. The controller of claim 14, wherein the identification element comprises an element or an inherent characteristic of the second segment.

16. The controller of claim 1, wherein the controller is further configured to control a direction of a current flow of the AC power waveform through the at least one heater wire part and/or a voltage polarity of the AC power waveform through the at least one heater wire part.

17. The controller of claim 16, wherein the at least one heater wire part is configured such that when a current flows in a first direction, only the first segment is powered and when the current flows in a second direction, both the first and second segments are powered.

18. The controller of claim 17, wherein the controller is further configured to adjust the application of the AC power waveform to the at least one heater wire part based on the selective reading of the at least one sensor.

19. The controller of claim 1, wherein the conduit comprises additional segments in addition to the first segment and the second segment.

20. The controller of claim 1, further comprising a multiplexor, and the at least one sensor comprising two or more sensors, the multiplexor coupled to the at least one sensor wire part to enable reading of a corresponding sensor of the two or more sensors.

* * * * *

UNITED STATES PATENT AND TRADEMARK OFFICE
CERTIFICATE OF CORRECTION

| | | |
|---|---|---|
| PATENT NO. | : 12,226,583 B2 | Page 1 of 1 |
| APPLICATION NO. | : 18/448477 | |
| DATED | : February 18, 2025 | |
| INVENTOR(S) | : Po-Yen Liu et al. | |

It is certified that error appears in the above-identified patent and that said Letters Patent is hereby corrected as shown below:

In the Specification

In Column 4, Line 42, delete "with a least a" and insert --with at least a--.

In Column 4, Line 45, delete "with a least a" and insert --with at least a--.

In Column 8, Line 15, delete "preferably 10 ms," and insert --preferably ±10 ms,--.

In Column 21, Line 44, delete "within +10%," and insert --within ±10%,--.

In Column 21, Line 44, delete "within +5%," and insert --within ±5%,--.

Signed and Sealed this
Twenty-third Day of September, 2025

John A. Squires
*Director of the United States Patent and Trademark Office*